(12) United States Patent
Yang et al.

(10) Patent No.: US 10,752,688 B2
(45) Date of Patent: Aug. 25, 2020

(54) ANTI-HUMAN TIM-3 ANTIBODIES AND METHODS OF USE THEREOF

(71) Applicant: Development Center for Biotechnology, New Taipei (TW)

(72) Inventors: Yu-Chen Yang, New Taipei (TW); Li-Yu Chen, Macau (MO); Chia-Hua Li, New Taipei (TW); Pei-Han Tai, New Taipei (TW); Hong-Kai Chen, New Taipei (TW); Ying-Yung Lok, New Taipei (TW); Chih-Yung Hu, New Taipei (TW); Chien-Tsun Kuan, New Taipei (TW); Chung-Hsiun Wu, New Taipei (TW)

(73) Assignee: DEVELOPMENT CENTER FOR BIOTECHNOLOGY, Taipei (TW)

( * ) Notice: Subject to any disclaimer, the term of this patent is extended or adjusted under 35 U.S.C. 154(b) by 0 days.

(21) Appl. No.: 15/859,506

(22) Filed: Dec. 30, 2017

(65) Prior Publication Data
US 2018/0186881 A1  Jul. 5, 2018

Related U.S. Application Data

(63) Continuation of application No. PCT/US2017/069140, filed on Dec. 30, 2017.

(60) Provisional application No. 62/440,290, filed on Dec. 29, 2016.

(51) Int. Cl.
| | |
|---|---|
| *C07K 16/00* | (2006.01) |
| *C07K 16/28* | (2006.01) |
| *A61P 35/00* | (2006.01) |
| *G01N 33/574* | (2006.01) |
| *A61K 39/00* | (2006.01) |

(52) U.S. Cl.
CPC .......... *C07K 16/2818* (2013.01); *A61P 35/00* (2018.01); *C07K 16/2803* (2013.01); *G01N 33/574* (2013.01); *G01N 33/57407* (2013.01); *A61K 2039/505* (2013.01); *A61K 2039/507* (2013.01); *C07K 2317/34* (2013.01); *C07K 2317/565* (2013.01); *C07K 2317/75* (2013.01); *C07K 2317/76* (2013.01); *C07K 2317/92* (2013.01); *G01N 33/57423* (2013.01); *G01N 33/57438* (2013.01); *G01N 2800/52* (2013.01)

(58) Field of Classification Search
None
See application file for complete search history.

(56) References Cited

U.S. PATENT DOCUMENTS 9,605,070 B2 * 3/2017 Sabatos-Peyton .......................... A61K 39/3955

OTHER PUBLICATIONS

Frank Immunology and Evolution of Infectious Disease, Chapter 4 "Specificity and Cross-Reactivity," Princeton University Press, 2002 (Year: 2002).*
van Regenmortel (Journal of Immunological Methods, 1998, 216:37-48) (Year: 1998).*

* cited by examiner

*Primary Examiner* — Meera Natarajan
(74) *Attorney, Agent, or Firm* — Liang Legal Group, PLLC

(57) ABSTRACT

An anti-human T-cell immunoglobulin domain and mucin domain 3 (TIM-3) antibody, can bind the peptides, comprising the amino-acid sequence RKGDVSL (SEQ ID NO: 9) and/or EKFNLKL (SEQ ID NO: 10) of human TIM-3 protein. The antibody can regulate immune cell activity. The antibody or binding fragment thereof is useful in diagnosis, prognosis, and treatment of cancers that have been reported to express cell-surface TIM-3 such as lung, liver, esophageal cancer and solid tumors.

8 Claims, 18 Drawing Sheets
Specification includes a Sequence Listing.

VH: (SEQ ID NO: 1)

EVQLQQSGPELVKPGASVKMSCKAS<u>GYTFTDYYMN</u>WVKQSHGKSLEWIG
(SEQ ID NO: 3)

<u>RVNPSNGGTNNQN</u>FKGKATLTVDKSLNTAYMQLNSLTSEDSAVYYCAR
(SEQ ID NO: 4)

<u>RDSSGYWFAY</u>WGQGTLVTVSA
(SEQ ID NO: 5)

VL: (SEQ ID NO: 2)

DIVMTQSHKFMSTSVGDRVSITC<u>KASQDVSTAVV</u>WYQQKPGQSPKILIF
(SEQ ID NO: 6)

<u>SPSYRYT</u>GVPDRFTGSGSGTEFTFTISSVQAEDLAVYYC<u>QQHYNIPWT</u>F
(SEQ ID NO: 7)                                                   (SEQ ID NO: 8)

GGGTKLEIRR

FIG. 1

| Mouse No. 10031196 | PC | NC | 1 4B10* | 2 CB6 | 3 1C3 | 4 2A7 | 5 8C11 | 6 BG5 | 7 BG1 | 8 3E4 | 9 3F10 | 10 9A11 | 11 5B10 | 12 9G11 | 13 BC12 |
|---|---|---|---|---|---|---|---|---|---|---|---|---|---|---|---|
| TIM-3 (22-202) | 1.36 | 0.05 | 0.81 | 0.82 | 0.75 | 0.73 | 0.91 | 0.81 | 0.74 | 0.88 | 0.93 | 0.97 | 0.68 | 0.74 | 0.74 |
| N1-CD40 (21-193) | 1.36 | 0.06 | 0.06 | 0.06 | 0.06 | 0.06 | 0.06 | 0.06 | 0.06 | 0.05 | 0.05 | 0.06 | 0.05 | 0.06 | 0.05 |

| Mouse No. 10031196 | 14 3D9 | 15 2F3 | 16 8H6 | 17 AG5 | 18 9E1 | 19 6F9 | 20 8C7 | 21 6C2 | 22 8B12 | 23 5D12 | 24 BG3 | 25 3A3 | 26 8D1 | 27 CH11 |
|---|---|---|---|---|---|---|---|---|---|---|---|---|---|---|
| TIM-3 (22-202) | 0.72 | 0.70 | 0.80 | 0.55 | 0.82 | 0.96 | 0.55 | 0.75 | 0.68 | 0.71 | 0.43 | 0.77 | 0.87 | 0.93 |
| N1-CD40 (21-193) | 0.05 | 0.05 | 0.05 | 0.05 | 0.05 | 0.05 | 0.05 | 0.06 | 0.06 | 0.06 | 0.06 | 0.06 | 0.05 | 0.05 |

Coating:
TIM-3 (22-202) Protein (His)  0.2 ug/well
N1-CD40 (21-193)  0.2 ug/well 1st Ab:
PC: Mouse Anti-Histidine tag  1000X
sup dilution 1X 2nd Ab:
Goat Anti-Mouse IgG-HRP  5000x Substrates:  OPD system
Exposure time: 5 min
Absorbent:  O.D 450

FIG. 2

FIG. 4C
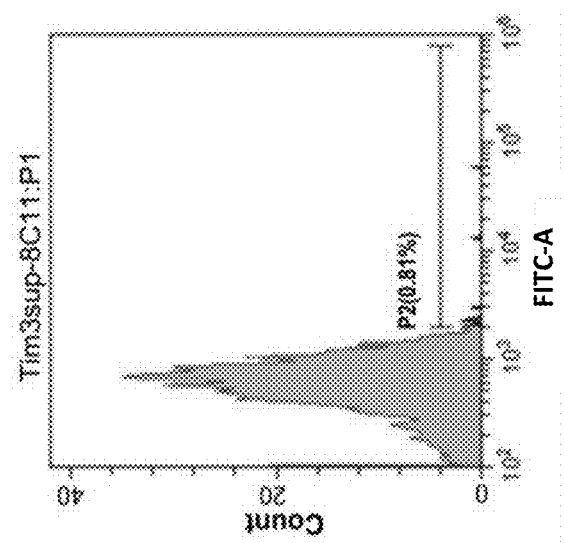
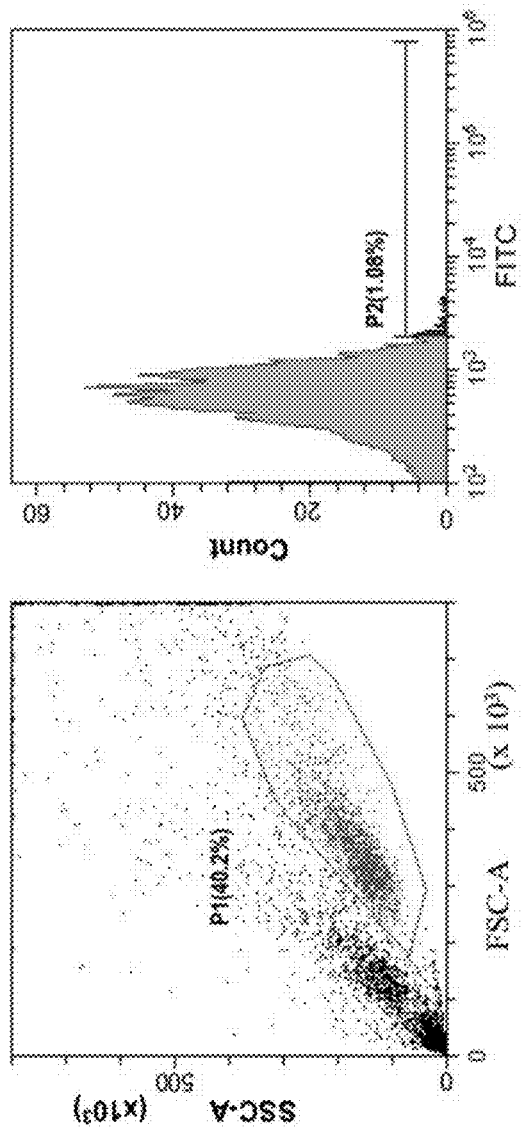
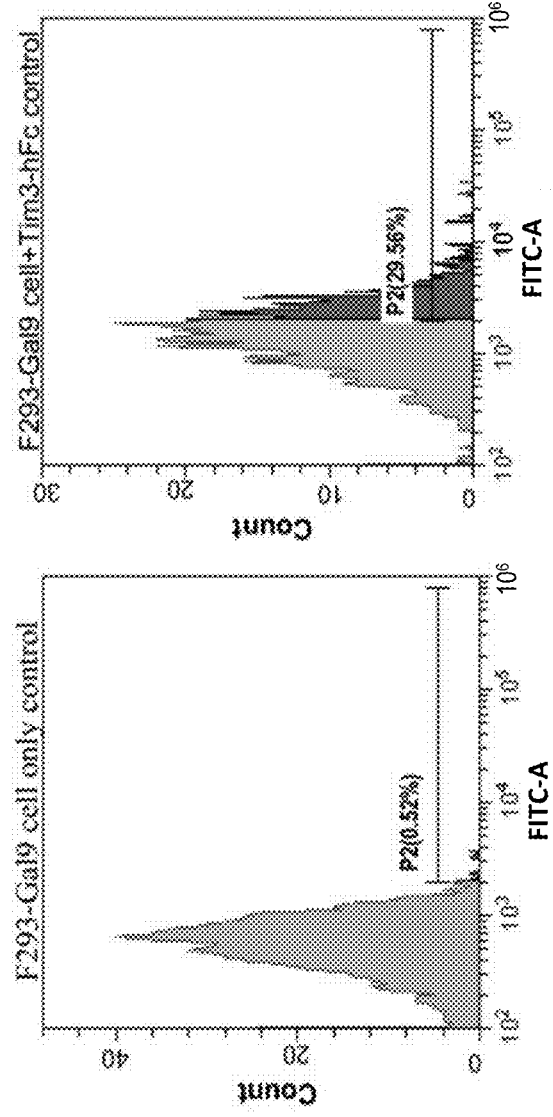

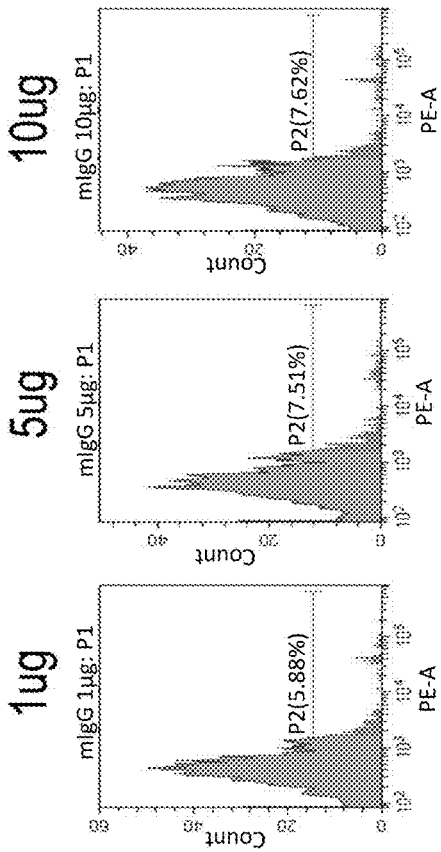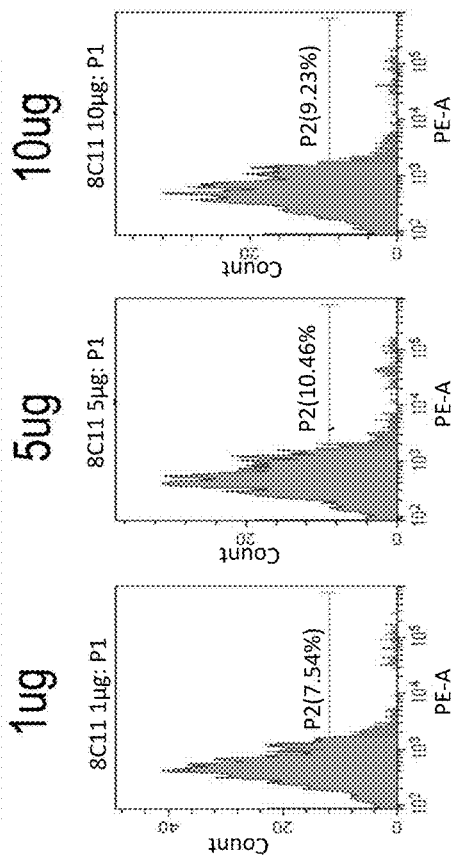
FIG. 6A

SEQUENCE LISTING

<160> NUMBER OF SEQ ID NOS: 10

<210> SEQ ID NO 1
<211> LENGTH: 119
<212> TYPE: PRT
<213> ORGANISM: Mus musculus

<400> SEQUENCE: 1

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
            35                  40                  45

Gly Arg Val Asn Pro Ser Asn Gly Gly Thr Asn Asn Gln Asn Phe
    50                  55                  60

Lys Gly Lys Ala Thr Leu Thr Val Asp Lys Ser Leu Asn Thr Ala Tyr
65                  70                  75                  80

Met Gln Leu Asn Ser Leu Thr Ser Glu Asp Ser Ala Val Tyr Tyr Cys
                85                  90                  95

Ala Arg Arg Asp Ser Ser Gly Tyr Trp Phe Ala Tyr Trp Gly Gln Gly
            100                 105                 110

Thr Leu Val Thr Val Ser Ala
        115

<210> SEQ ID NO 2
<211> LENGTH: 108
<212> TYPE: PRT
<213> ORGANISM: Mus musculus

<400> SEQUENCE: 2

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Val Trp Tyr Gln Gln Lys Pro Gly Gln Ser Pro Lys Ile Leu Ile
            35                  40                  45

Phe Ser Pro Ser Tyr Arg Tyr Thr Gly Val Pro Asp Arg Phe Thr Gly
    50                  55                  60

Ser Gly Ser Gly Thr Glu Phe Thr Phe Thr Ile Ser Ser Val Gln Ala
65                  70                  75                  80

Glu Asp Leu Ala Val Tyr Tyr Cys Gln Gln His Tyr Asn Ile Pro Trp
                85                  90                  95

Thr Phe Gly Gly Gly Thr Lys Leu Glu Ile Arg Arg
            100                 105

<210> SEQ ID NO 3
<211> LENGTH: 10
<212> TYPE: PRT
<213> ORGANISM: Mus musculus

<400> SEQUENCE: 3

Gly Tyr Thr Phe Thr Asp Tyr Tyr Met Asn
1               5                   10

<210> SEQ ID NO 4
<211> LENGTH: 17
<212> TYPE: PRT
<213> ORGANISM: Mus musculus

```
<400> SEQUENCE: 4

Arg Val Asn Pro Ser Asn Gly Gly Thr Asn Asn Asn Gln Asn Phe Lys
1               5                   10                  15

Gly

<210> SEQ ID NO 5
<211> LENGTH: 10
<212> TYPE: PRT
<213> ORGANISM: Mus musculus

<400> SEQUENCE: 5

Arg Asp Ser Ser Gly Tyr Trp Phe Ala Tyr
1               5                   10

<210> SEQ ID NO 6
<211> LENGTH: 11
<212> TYPE: PRT
<213> ORGANISM: Mus musculus

<400> SEQUENCE: 6

Lys Ala Ser Gln Asp Val Ser Thr Ala Val Val
1               5                   10

<210> SEQ ID NO 7
<211> LENGTH: 7
<212> TYPE: PRT
<213> ORGANISM: Mus musculus

<400> SEQUENCE: 7

Ser Pro Ser Tyr Arg Tyr Thr
1               5

<210> SEQ ID NO 8
<211> LENGTH: 9
<212> TYPE: PRT
<213> ORGANISM: Mus musculus

<400> SEQUENCE: 8

Gln Gln His Tyr Asn Ile Pro Trp Thr
1               5

<210> SEQ ID NO 9
<211> LENGTH: 7
<212> TYPE: PRT
<213> ORGANISM: Homo sapiens

<400> SEQUENCE: 9

Arg Lys Gly Asp Val Ser Leu
1               5

<210> SEQ ID NO 10
<211> LENGTH: 7
<212> TYPE: PRT
<213> ORGANISM: Homo sapiens

<400> SEQUENCE: 10

Glu Lys Phe Asn Leu Lys Leu
1               5
```

ANTI-HUMAN TIM-3 ANTIBODIES AND METHODS OF USE THEREOF

CROSS REFERENCE TO RELATED APPLICATIONS

This claims the benefit of PCT/US2017/069140, filed on Dec. 30, 2017, which claims the benefit of Provisional Application No. 62/440,290, filed on Dec. 29, 2016. The disclosures of these prior application are incorporated by reference in their entirety.

BACKGROUND OF INVENTION

Field of the Invention

The present invention relates to methods for generation and use of antibodies that bind specifically to the human T-cell immunoglobulin domain and mucin domain 3 (TIM-3).

Background Art

Immune responses play important roles in staving off cancer. Therefore, T cell exhaustion may be associated with tumor growth in hosts. T cell exhaustion may arise from many mechanisms. A programmed cell death molecule (PD-1) is a marker of the exhausted T cells. Blockade of PD-1 interactions with its ligand (PD-1 ligand, or PD1L) can partially restore T cell function.

In addition to PD-1, T cell immunoglobulin mucin 3 (TIM-3) expression was found on CD8$^+$ tumor-infiltrating lymphocytes in mice bearing solid tumors. TIM-3 was originally found to be a T helper (Th) 1-specific type I membrane protein. TIM-3, an immune checkpoint, regulates macrophage activation and plays a vital role in Th1 immunity and tolerance induction.

All TIM-3 expressing tumor-infiltrating lymphocytes are also found to express PD-1. These TIM-3 and PD-1 expressing lymphocytes account for a major fraction of T cells that infiltrate tumors. In addition, these TIM-3 and PD-1 expressing lymphocytes also exhibit the most severe exhausted phenotype: they fail to proliferate and also fail to produce IL-2, TNF, and IFN-γ. (Sakuishi et al., J. Exp. Med., 2010, 207(10): 2187-2194).

More recently, TIM-3 has also been found to play a role in the regulation of other cells, such as Th17 cells, CD4(+) CD25(+) regulatory T cells ($T_{reg}$s), CD8(+) T cells and certain innate immune cells.

Because the TIM-3 pathway is involved in the pathogenesis of autoimmune diseases, chronic viral infections, and cancers, there is a need to find agents that can inhibit or block the TIM-3 signaling pathway.

SUMMARY OF INVENTION

Embodiments of the invention relate to antibodies that can bind specifically with TIM-3, thereby inhibiting the functions of TIM-3. TIM-3 signaling pathway is found to be associated with T cell exhaustion. Therefore, antibodies of the invention can be used to prevent or treat diseases or conditions associated with T cell exhaustion, such as autoimmune dieases and cancers.

One aspect of the invention relates to anti-human T-cell immunoglobulin domain and mucin domain 3 (TIM-3) antibodies, or a binding fragment (e.g., scFv, Fab, or (Fab)$_2$) thereof. An anti-human T-cell immunoglobulin domain and mucin domain 3 (TIM-3) antibody, or a binding fragment thereof, in accordance with one embodiment of the invention, can bind an epitope consisting of the sequence of RKGDVSL (SEQ ID NO: 9) and/or EKFNLKL (SEQ ID NO: 10) in TIM-3. The dissociation constant (Kd) of the antibody or the binding fragment thereof may be 10 nM or lower. The antibody or the binding fragment thereof can regulate human immune cell activity via TIM-3

An anti-human T-cell immunoglobulin domain and mucin domain 3 (TIM-3) antibody, or a binding fragment thereof, in accordance with embodiments of the invention, may comprise a heavy-chain variable domain having the following complementarity determining region (CDR) sequences: HCDRI (SEQ ID NO: 3), HCDR2 (SEQ ID NO: 4), HCDR3 (SEQ ID NO: 5), and/or a light-chain variable domain having the following CDR sequences: LCDR1 (SEQ ID NO: 6), LCDR2 (SEQ ID NO: 7), and LCDR3 (SEQ ID NO: 8).

An anti-human T-cell immunoglobulin domain and mucin domain 3 (TIM-3) antibody, or a binding fragment thereof, in accordance with embodiments of the invention, may comprise a heavy chain having the sequence of SEQ ID NO: 1 and/or a light chain having the sequence of SEQ ID NO: 2.

In accordance with embodiments of the invention, an antibody, or the binding fragment thereof, can induce T cells to secrete cytokines comprising IFN-γ and/or TNF-α. In accordance with some embodiments of the invention, an antibody may be a monoclonal antibody.

In accordance with embodiments of the invention, an antibody, or a binding fragment thereof, of the invention is useful in diagnosis, prognosis, and treatment of cancers that express cell-surface TIM-3. These cancers, for example, may include lung, liver, esophageal cancer, and solid tumors.

Other aspects and advantages of the invention will be apparent from the following description and the appended claims.

BRIEF DESCRIPTION OF DRAWINGS

FIG. 1 shows the sequences of the heavy chain and light chain variable regions of a monoclonal anti-human TIM-3 antibody, 8C11 in accordance with one embodiment of the invention. The complementarity determining region (CDR) sequences are shown as bold-faced and underlined sequences. The framework sequences are dispersed between and flanking the CDR sequences.

FIG. 2 shows the binding activities of various anti-human TIM-3 antibodies. These results summarize the binding data for the murine antibody 8C11 and other TIM-3 binding antibodies.

FIG. 4C shows that anti-human TIM-3 antibody 8C11 can block (compete with) the binding of TIM-3 hFc with Galectin-9.

FIG. 6A-6B show that TIM-3 mAb 8C11 does not induce human CD4+ T cell death.

DEFINITIONS

Figure 3A:
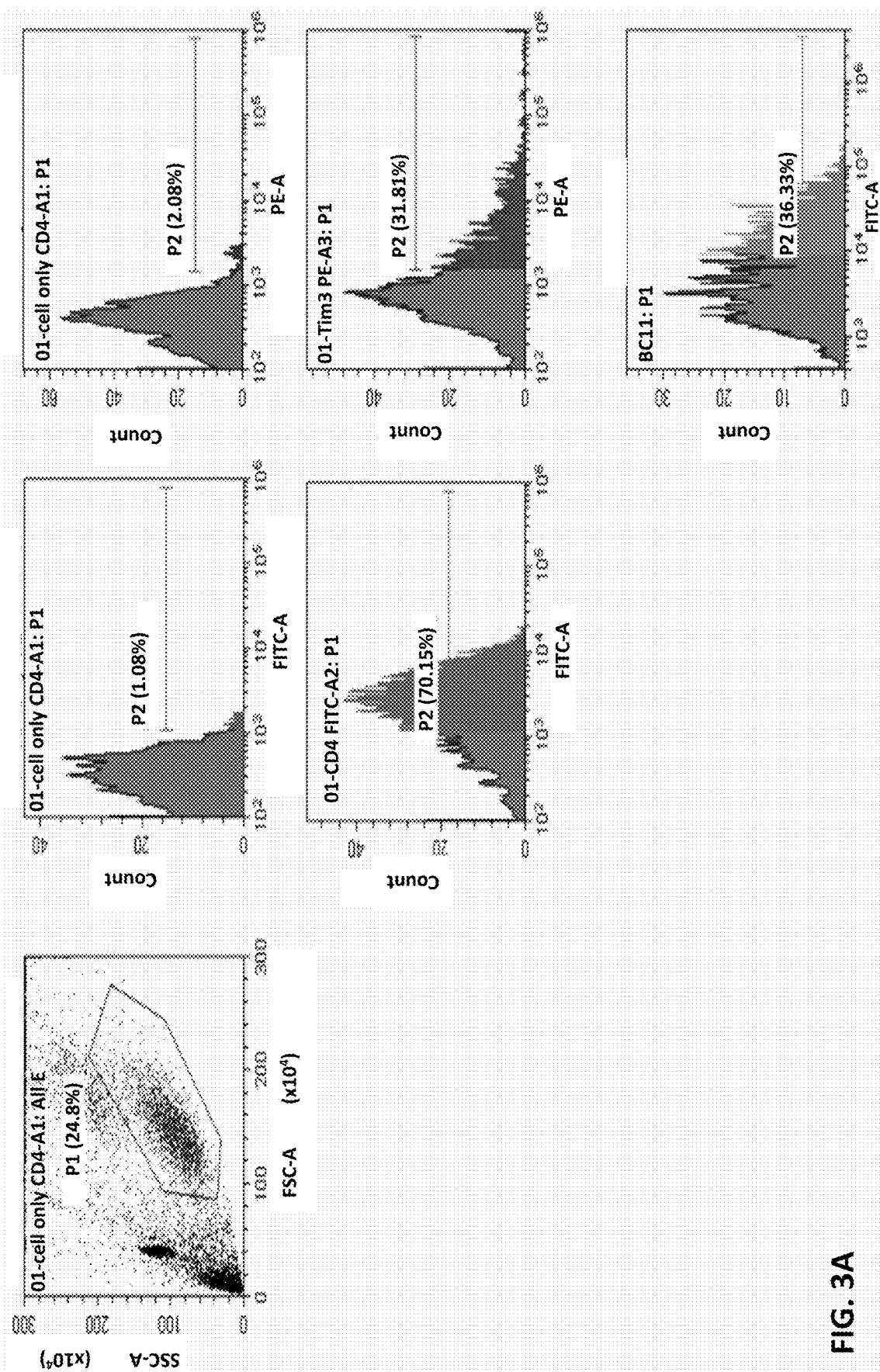
FIG. 3A and FIG. 3B show that monoclonal antibody 8C11 binding to human CD4 or CD8 T cells in FACS assays, respectively. These results show that 8C11 is capable of binding the CD4+ and CD8+ T cells.

As used herein, "complementarity-determining region (CDR)" refers to the three hypervariable sequences in the variable region that are involved in antigen recognition. The three CDRs are dispersed by four "framework" regions in the light or heavy chain variable region. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. These may be abbreviated as HCDR1, HCDR2, HCDR3, LCDR1, LCDR2, and LCDR3, respectively, wherein H denotes the heavy chain and L denotes the light chain.

The sequences of the framework regions (FR) of different light or heavy chains are relatively conserved within a species. The framework region of an antibody, that is the combined framework regions of the constituent light and heavy chains, serves to position and align the CDRs in three-dimensional space. The four FRs that flank the 3 CDRs may be referred to as FR1, FR2, FR3, and FR4.

The amino acid sequences of the CDRs and framework regions (FRs) can be determined using various well-known definitions in the art, e.g., Kabat, Chothia, international ImMunoGeneTics database (IMGT), and AbM (see, e.g., Johnson et al., supra; Chothia & Lesk, (1987) J. Mol. Biol. 196, 901-917; Chothia et al. (1989) Nature 342, 877-883; Chothia et al. (1992) J. Mol. Biol. 227, 799-817; Al-Lazikani et al., J. Mol. Biol. 1997, 273(4)). Definitions of antigen combining sites are also described in the following: Ruiz et al. Nucleic Acids Res., 28, 219-221 (2000); and Lefranc Nucleic Acids Res. January 1; 29 (1):207-9 (2001); Mac-Callum et al., J. Mol. Biol., 262: 732-745 (1996); and Martin et al, Proc. Natl. Acad. Sci. USA, 86, 9268-9272 (1989); Martin, et al, Methods Enzymol., 203: 121-153, (1991); Pedersen et al, Immunomethods, 1, 126, (1992); and Rees et al, In Sternberg M. J. E. (ed.), Protein Structure Prediction. Oxford University Press, Oxford, 141-172 1996).

The antibody binds to an "epitope" on the antigen. An epitope is a specific antibody binding interaction site on the antigen, and an epitope can include a few amino acids or portions of a peptide fragment. For example, an epitope may include a stretch of peptide of 5 or 6 or more amino acid residues.

DETAILED DESCRIPTION

Embodiments of the invention relate to antibody molecules that specifically bind with human TIM-3. These anti-human TIM-3 antibody molecules can be used to treat, and/or diagnose immune or cancerous diseases.

Immune responses play important roles in staving off cancer. However, in chronic viral infections and cancers, it has been found that T cell exhaustion is associated with these diseases. T cell exhaustion may arise from many mechanisms. A programmed cell death molecule (PD-1) is a marker of the exhausted T cells. Blockade of PD-1 interactions with its ligand (PD-1 ligand, or PD1L) can partially restore T cell function.

In addition to PD-1, T cell immunoglobulin mucin 3 (TIM-3), which is an immune checkpoint marker, is also found to be involved in T cell exhaustion. TIM-3 was originally found to be a T helper (Th) 1-specific type I membrane protein. TIM-3, an immune checkpoint, regulates macrophage activation and plays a vital role in Th1 immunity and tolerance induction.

TIM-3 expression was also found on CD8$^+$ tumor-infiltrating lymphocytes in mice bearing solid tumors. All TIM-3 expressing tumor-infiltrating lymphocytes are also found to express PD-1. These TIM-3 and PD-1 expressing lymphocytes account for a major fraction of the T cells that infiltrate tumors. In addition, these TIM-3 and PD-1 expressing lymphocytes also exhibit the most severe exhausted phenotype: they fail to proliferate and also fail to produce IL-2, TNF, and IFN-γ. (Sakuishi et al., J. Exp. Med., 2010, 207(10): 2187-2194).

More recently, TIM-3 has been found to play a role in the regulation of other cells, such as Th17 cells, CD4(+) CD25 (+) regulatory T cells ($T_{reg}$s), CD8(+) T cells and certain innate immune cells. Because the TIM-3 pathway is involved in the pathogenesis of autoimmune diseases, chronic viral infections and cancers, antibodies of the invention can be used in the treatments of these disease.

In accordance with embodiments of the invention, several clones of antibodies against human TIM-3 were generated. The variable domain sequences were determined.

One exemplary antibody, 8C11, has been further investigated. The epitopes on the extracellular domain of TIM-3 for 8C11 are found to be in the regions of RKGDVSL and/or EKFNLKL. It was found that 8C11 can bind with TIM-3, can interfere with the interactions between TIM-3 and its ligand, Galectin-9. In addition, 8C11 binding to TIM-3 does not induce T cell death, i.e., binding of the antibody to TIM-3 does not trigger the TIM-3 signaling pathway. Therefore, there is no risk of inducing T cell exhaustion by an antibody of the invention.

In addition, antibodies of the invention can enhance IFN-γ and TNF-α sections by T cell, thereby enhancing immune responses. These antibodies are able to suppress tumor growths in animal models. Therefore, antibodies of the invention can be used to treat cancers, such as lung, breast, pancreas, liver, colorectal, or prostate cancer.

Embodiments of the invention will be illustrated with the following examples. One skilled in the art would appreciate that these examples are for illustration only and other modifications and variations are possible without departing from the scope of the invention.

Example 1: Generation of Anti-Human TIM-3 Monoclonal Aantibodies

To generate a monoclonal antibody against human TIM-3, BALB/c mice were primed with purified recombinant human TIM-3 antigen (as a fusion protein with a 6×His tag). The splenocytes were harvested and then cultured after fusing with Fo cells. The hybridoma cells secreting monoclonal antibodies that can recognize TIM-3 antigen were selected by a TIM-3 antigen-based ELISA. The selected clones were verified by FACS assays. Many clones were isolated and analyzed as described below.

Example 2: Binding of Anti-TIM-3 Aantibody 8C11 to CD4+ and CD8+ T Cells

Whether these antibodies can recognize the native TIM-3 molecules on cell surface was assessed by FACS analysis. In these tests, CD4 T cells and CD8 T cells were stimulated with CD3/CD28 dynamic beads to induce TIM-3 expression. These cells were then stained with cell markers CD4-FITC, CD8-APC, and TIM-3 PE (2E2), respectively, as controls.

Figure 3B:
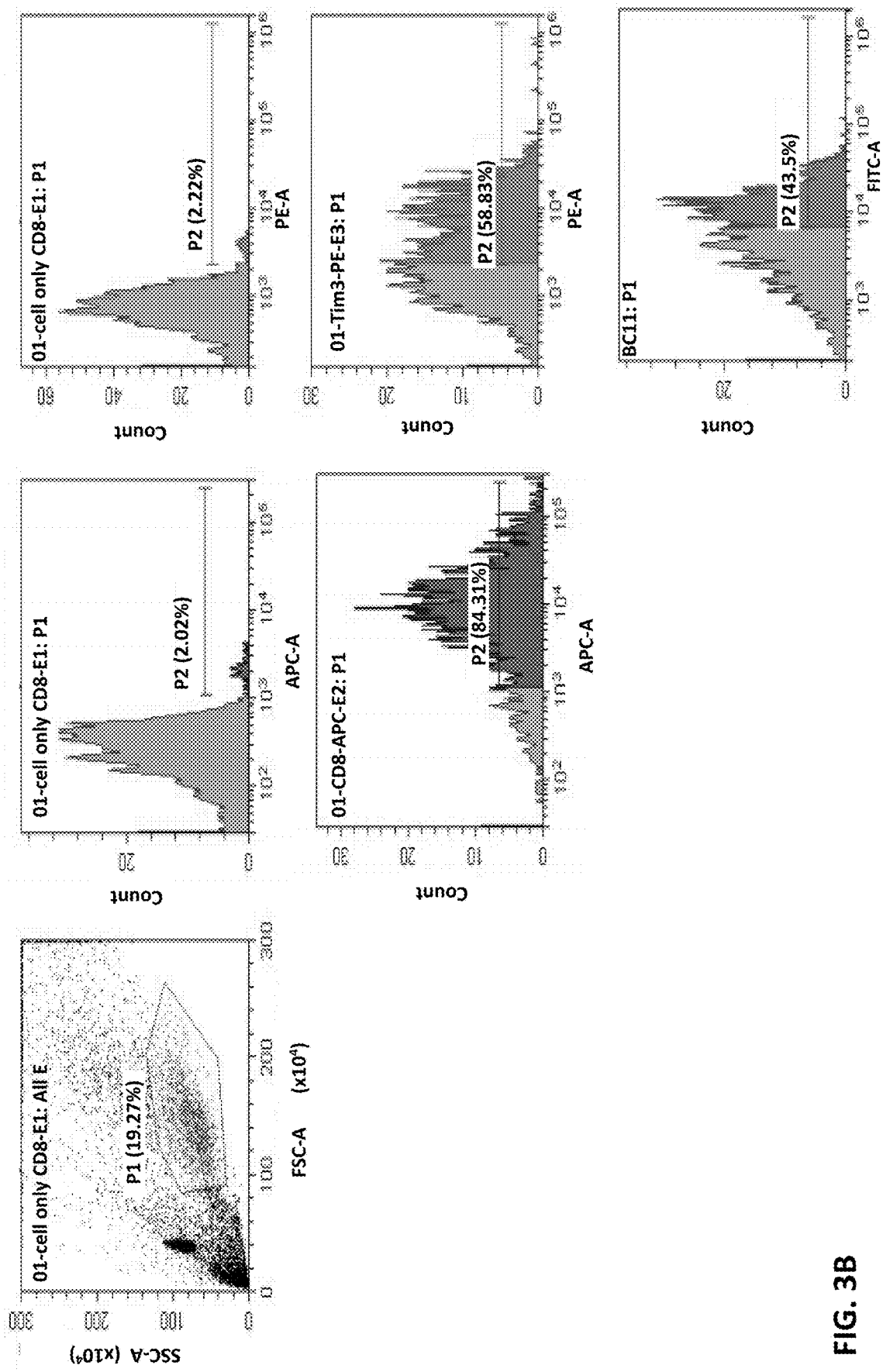

FIG. 3A shows results of monoclonal antibody 8C11 binding to human CD4 T cells, and FIG. 3B shows results of monoclonal antibody 8C11 binding to human CD8 T cells. These results show that TIM-3 expression on human CD4 or CD8 T cells can be detected by anti-TIM-3 monoclonal antibody 8C11. That is, the anti-TIM-3 antibody 8C11 can recognize the native TIM-3 on cell surfaces.

Example 3: The Human TIM-3 Binding ELISA of 27 Antibody Clones

To analyze the TIM-3 binding abilities of 27 antibody clones isolated above, the individual hybridoma clones were amplified in 3 ml culture supernatant. These culture supernatants were diluted 1× for the further analysis. Human TIM-3 protein, expressed as a protein having residues 22-202 of TIM-3 with a His-tag, was coated on a 96-well ELISA plate (0.2 μg/well) and CD40, expressed as a peptide having residues 21-193 of CD40, was coated on in the well at 0.2 μg/well and used as a negative control. A mouse anti-histidine tag antibody was used as a positive control.

After binding of the antibody clones, a goat anti mouse IgG conjugated with horse radish peroxidase (HRP) was used as a second antibody and 3,3',5,5'-Tetramethylbenzidine (TMB) was used as a substrate to assess the antibody-TIM-3 bindings. The OD405 was read to calculate the activities and the results are shown in FIG. 2.

As shown in FIG. 2, several clones have good affinities in binding TIM-3, including 8C11, 3F10, 9A11, 6F9, and CH11, which all have binding activities (OD450>0.9 in this assay). Most of the following experiments use 8C11 clone as an example. However, one skilled in the art would appreciate that other antibodies having reasonable binding affinities can also be used. Therefore, the scope of the invention is not limited to the 8C11 clone or any particular examples described herein.

Example 4: Anti-Human TIM-3 Antibody 8C11 Interrupts Galectin-9/TIM-3 Binding on F293 Cells To assess the abilities of anti-human TIM-3 antibodies to interrupt Galectin-9/TIM-3 binding, an F293 cell-based assay was set up. The Galectin-9 gene was cloned into a mammalian expression vector. The gene of human TIM-3 extracellular domain was cloned and fused with a human IgG1 Fc domain. The fused gene was then cloned into a mammalian expression vector. To generate a Galectin-9 expressing F293 cell line and to produce the recombinant protein of human TIM-3 extracellular domain, transfection kits were used to introduce the plasmids into F293 cells, and stable transformants were then selected with G418 treatment.

Figure 4A:
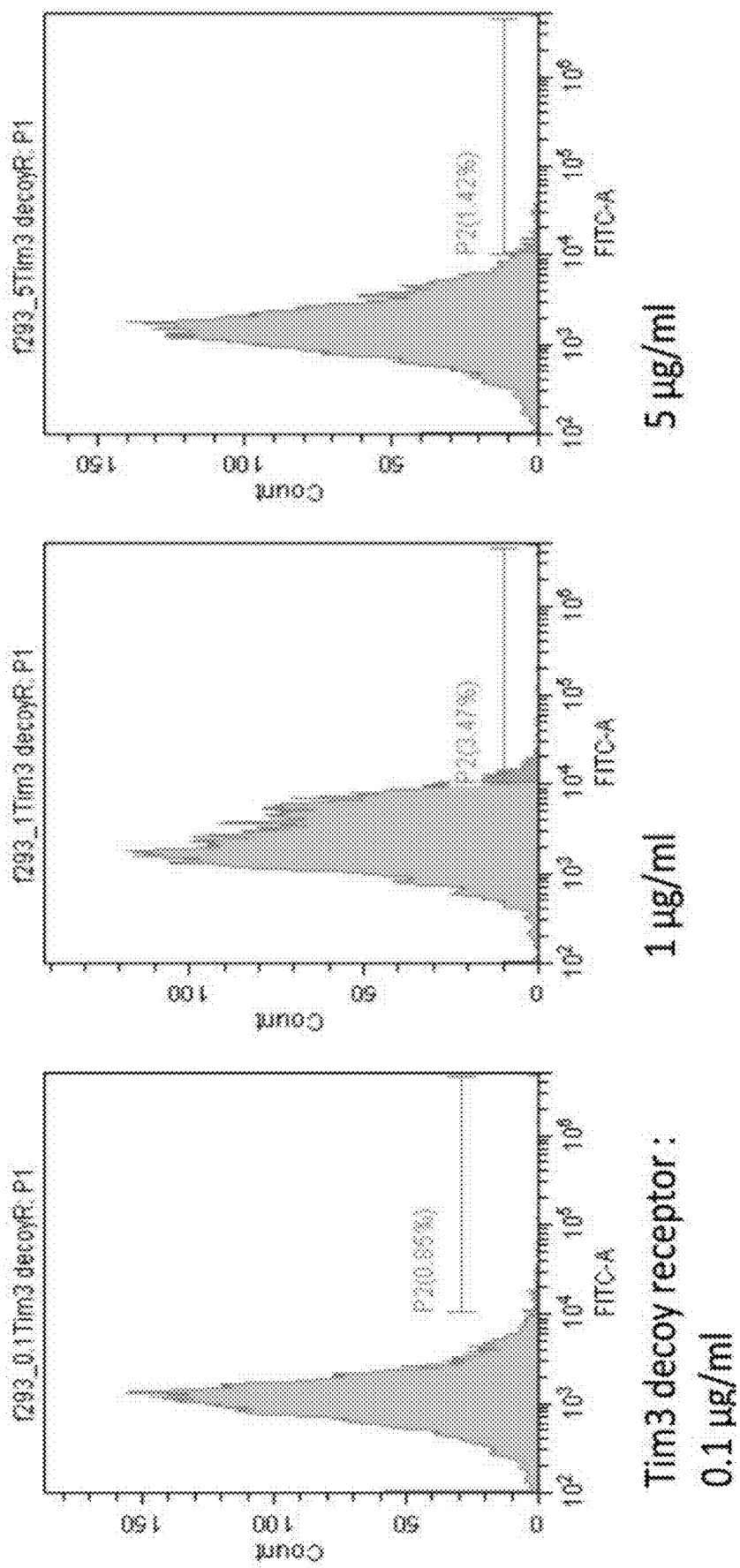
FIG. 4A shows that the human TIM-3-hFc recombinant protein (Tim3 decoy receptor) cannot bind F293 cells prior to Galectin-9 transfection.
Figure 4B:
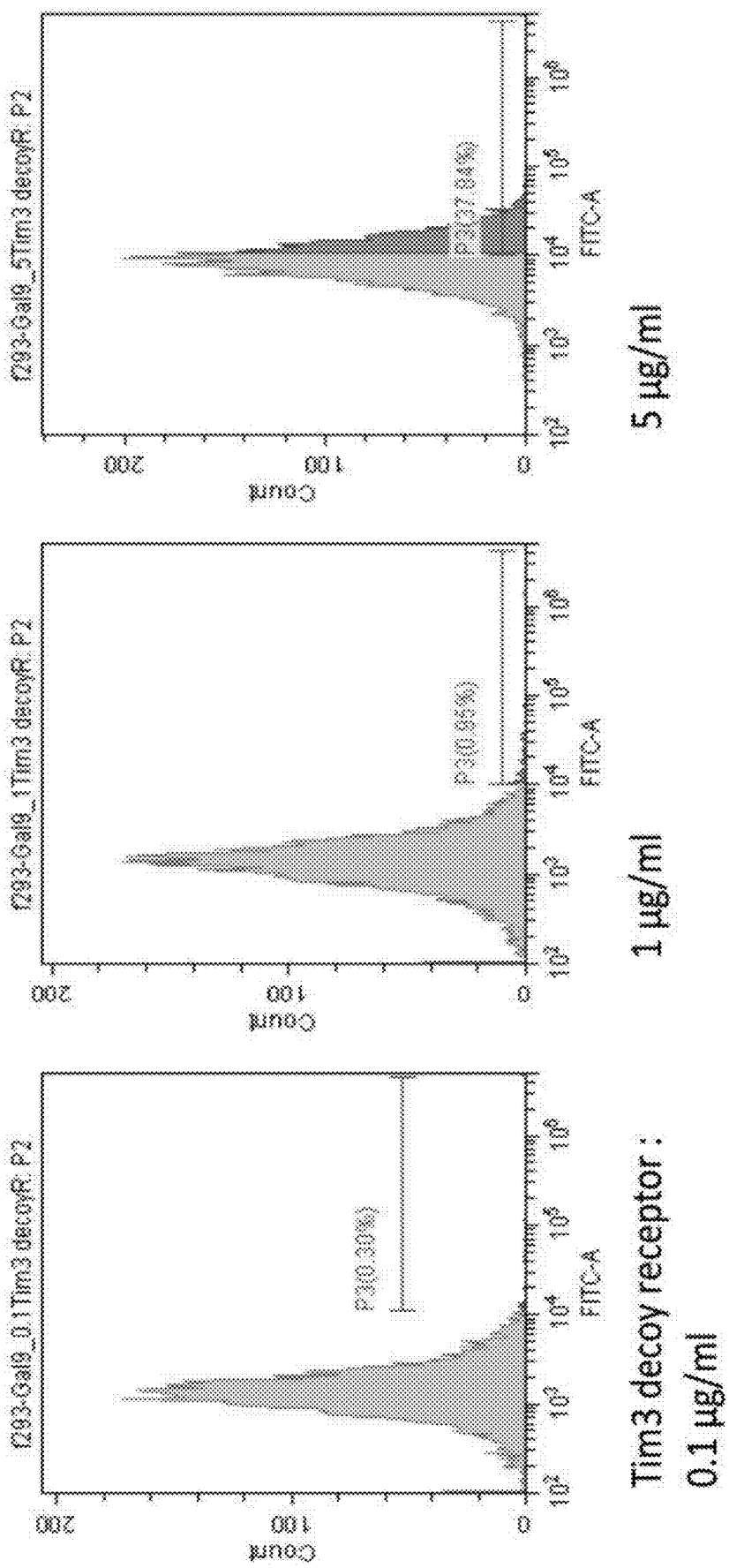
FIG. 4B shows that the human TIM-3-hFc recombinant protein can bind F293 cells transfected with Galectin-9 in a FACS assay.

The assay system was set-up as a competition assay. The results are shown in FIG. 4A-FIG. 4C. FIG. 4A shows that F293 cells prior to transfection with Galectin-9 did not bind with TIM-3 decoy (i.e., recombinant TIM-3 extracellular domain fused with a human IgG1 Fc domain). FIG. 4B shows that after transfection with Galectin-9, the F293 cells can bind with the cells expressing the recombinant TIM-3 extracellular domain fused with a human IgG1 Fc domain. In FIG. 4C, the results show that the anti-human TIM-3 antibody 8C11 can compete with the Galectin-9/TIM-3 binding. Therefore, the anti-human TIM-3 antibody 8C11 can be used to interfere with the signaling pathways mediated by TIM-3, thereby inhibiting Galecting-9 or TIM-3 functions.

Example 5: Anti-Human TIM-3 Antibody 8C11 can Reduce Human T Cell Death by Interrupting Galectin-9/TIM-3 Binding The signaling pathway of Galectin-9/TIM-3 in human T cell can induce cell death and reduce the T cell activity. To investigate whether anti-human TIM-3 antibody 8C11 can block the Galectin-9/TIM-3 signal pathway, a Galectin-9 induced T cell death model was generated. An IgG antibody from a normal mouse was used as a negative control and a monoclonal antibody 2E2 was used as a positive control. CD25 is used as a human T cell early activation marker.

Figure 5:
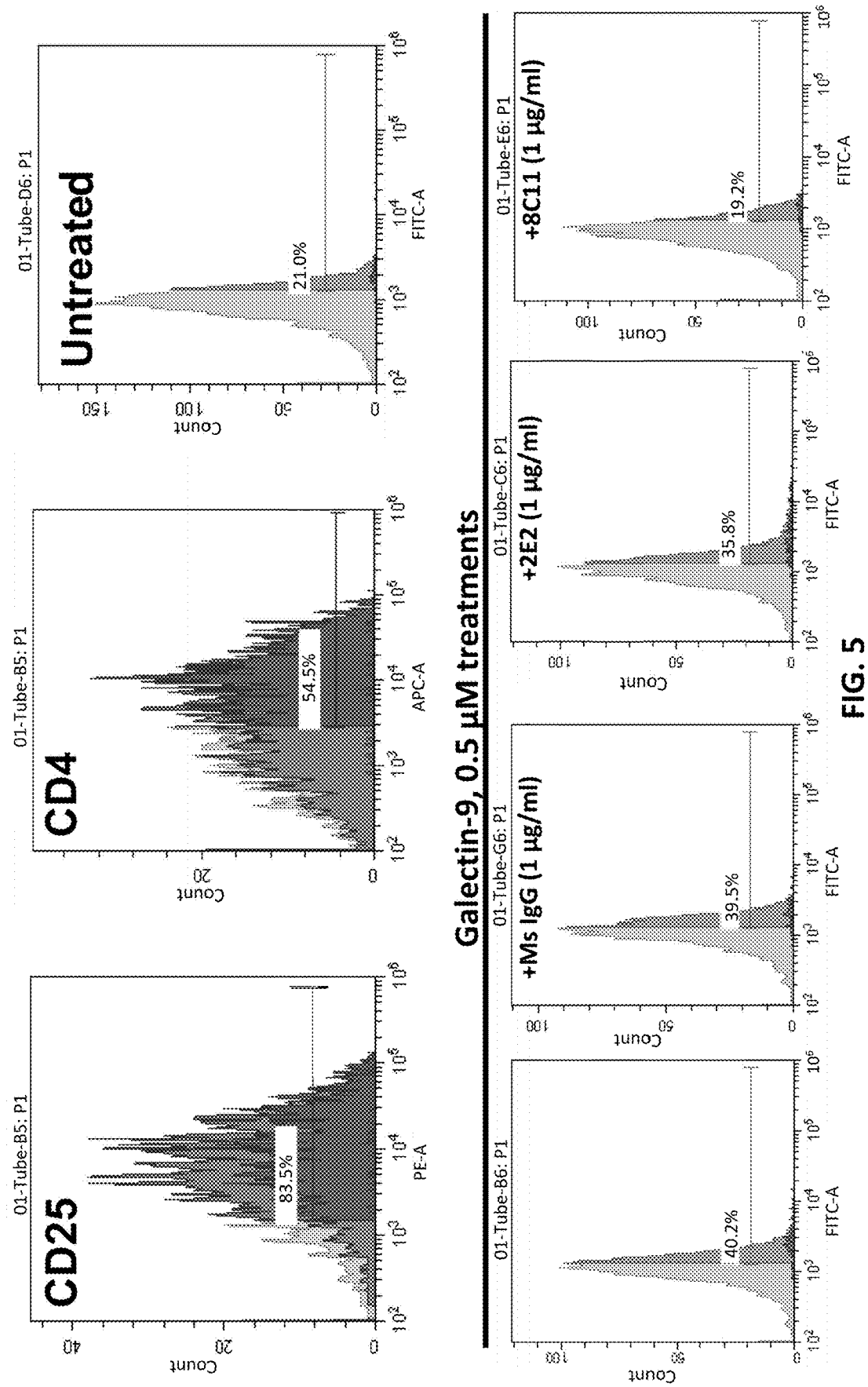
FIG. 5 shows that anti-human TIM-3 antibody 8C11 can block the binding of Galectin-9 to human CD4 T cell, thereby reducing apoptosis.

The results of this T cell death assay are shown in FIG. 5. As shown in FIG. 5, Galectin-9 treatment induced about 40.2% CD4+CD25+ T cells, which are regulatory T cells having immune suppressive effects. Addition of control IgG did not substantially affect the induction of this population of T cells, whereas addition of anti-TIM-3 antibody 2E2 resulted in some decrease of this population of T cells to 35.8%. In contrast, addition of an anti-TIM-3 antibody of the invention (8C11) resulted in markedly decreased (19.2%) CD4+CD25+ T cell population.

These results indicate that anti-human TIM-3 antibody 8C11 can block Galectin-9/TIM-3 signaling in human T cell to reduce human T cell death. Thus, anti-human TIM-3 antibody 8C11 can be used to treat diseases and/or conditions mediated by Galectin-9/TIM-3 signaling.

Example 6: Anti-Human TIM-3 Antibody 8C11 does not Induce T Cell Death

Because 8C11 can bind to TIM-3, it may or may not trigger the signaling pathway of the TIM-3 receptor. To investigate whether anti-human TIM-3 antibody 8C11 can interact with human T cell and trigger its signaling leading to cell death, we isolated human CD4+ and CD8+ T cells, and induced cell differentiation with CD3, CD28, and/or anti-IL4, IL-12. CD25 is used as a human T cell early activation marker. Propidium iodide (PI) stain is used to assess cell death. With FACS analysis, anti-human TIM-3 antibody 8C11 was found not to induce T cell death.

Figure 6B:
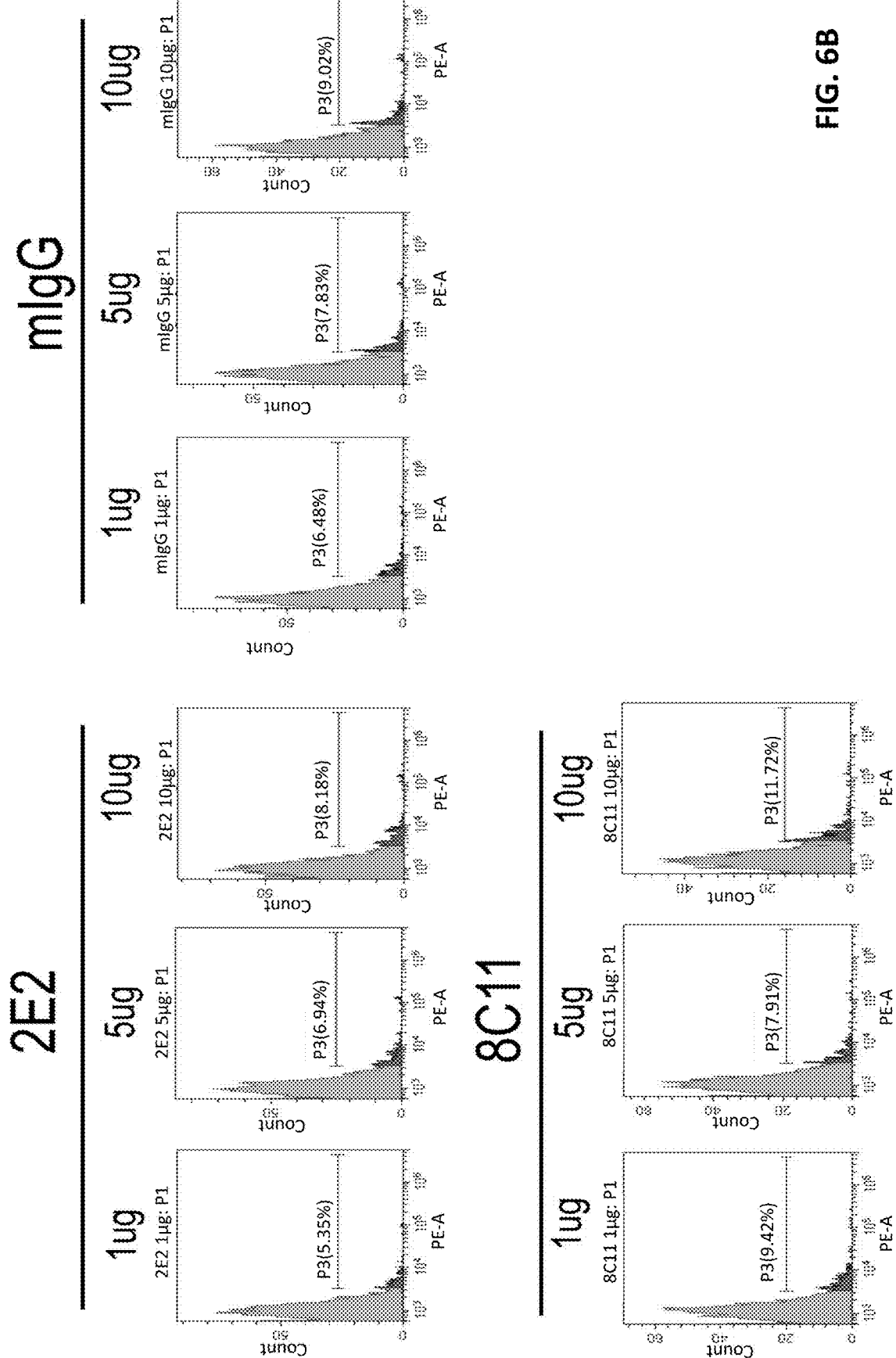
Figure 6C:
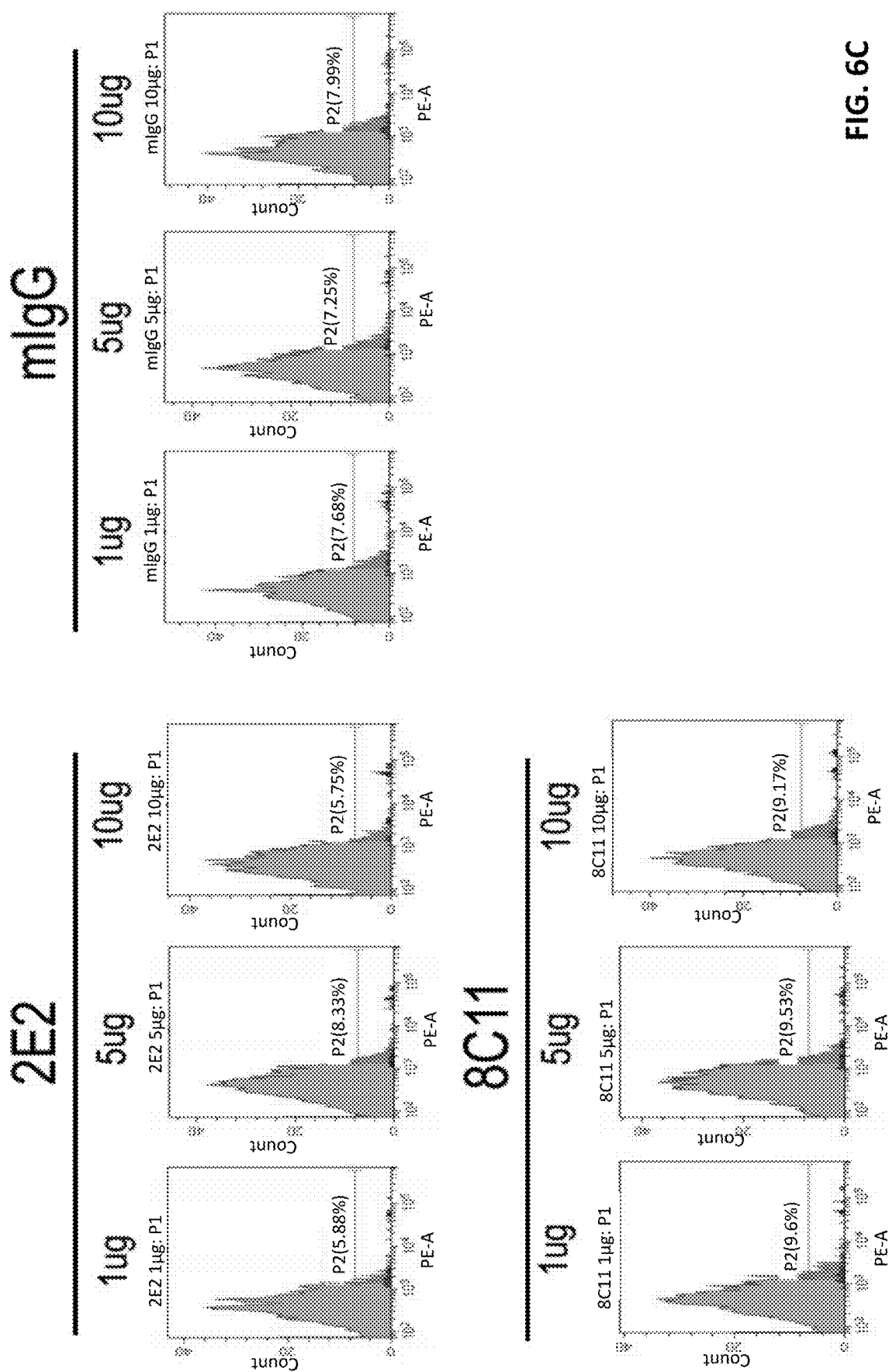
FIG. 6C-6D show that TIM-3 mAb 8C11 does not induce human CD8+ T cell death.
Figure 6D:
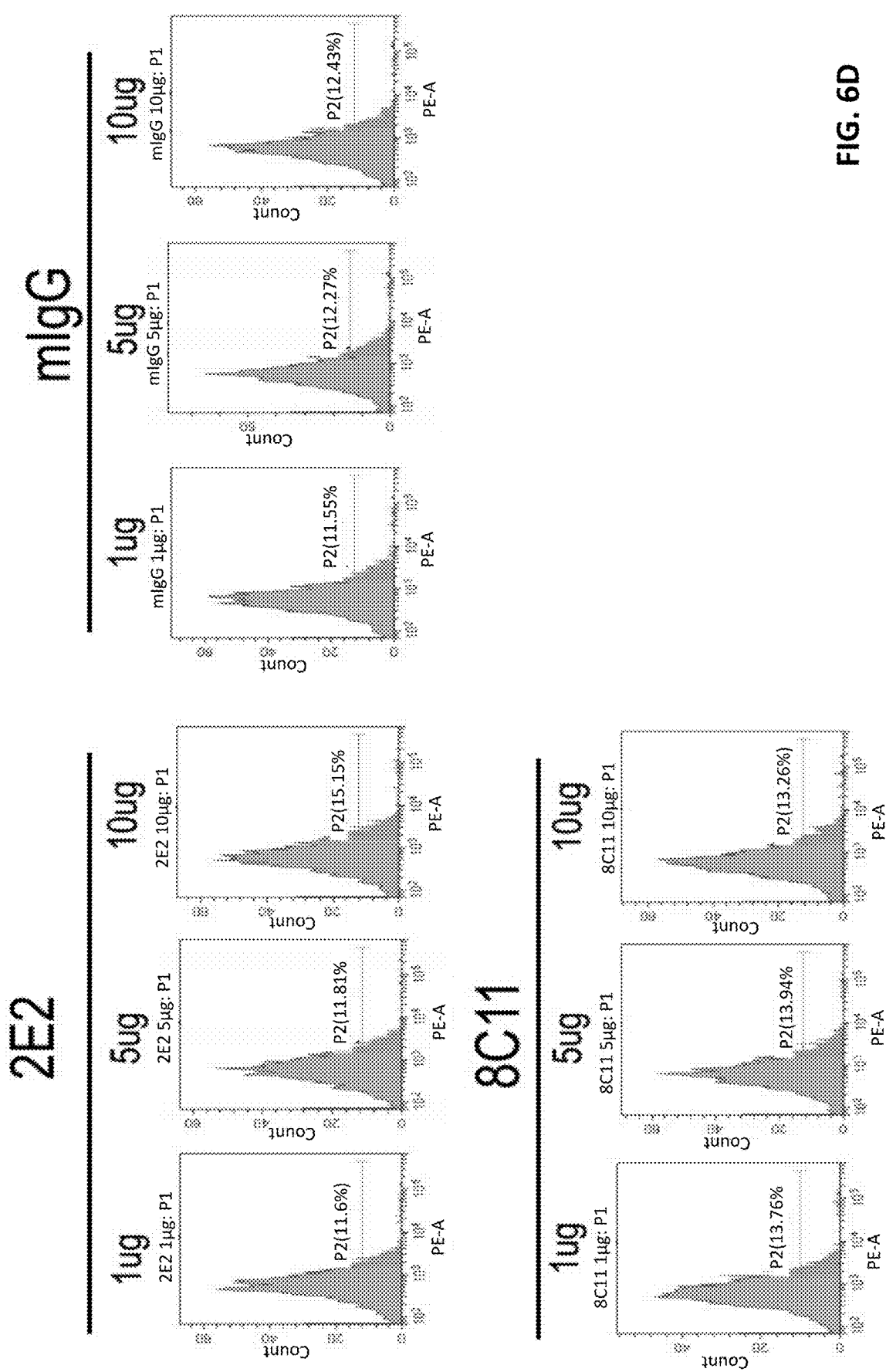

As shown in FIG. 6A and FIG. 6B, anti-TIM-3 antibody 8C11 produced similar effects as those of the control antibodies, mIgG and anti-TIM-3 2E2. This observation suggests that antibody 8C11 does not induce human CD4+ T cell death. In addition, anti-TIM-3 antibody 8C11 also does not induce human CD8+ T cell death, as shown in FIG. 6C and FIG. 6D, as evidenced by the similar patterns as the control antibodies, mIgG and mAb 2E2.

Therefore, 8C11 can bind to TIM-3 without triggering the signaling pathways mediated by TIM-3. As noted above, 8C11 can bock the interactions between Galectin-9 and TIM-3. Accordingly, 8C11 can be used as a therapeutic agent to treat TIM-3 mediated diseases or conditions without concerns of inducing T cell exhaustion.

Example 7: The Epitopes on TIM-3

To determine the epitopes that bind the antibody, hydrogen-deuterium exchanges in a recombinant protein were measured by using pepsin-digested fragments and HDX MS method in the presence and absence of the mouse monoclonal antibody.

The recombinant protein (15 pmol) and protein-antibody complex (15 pmol: 10 pmol) were diluted in an exchange buffer (99.9% D20 in PBS, pH 7.4) at 1:10 ratio to initiate the HD exchange at room temperature. At 7 time points (10s, 30s, 60s, 300s, 600s, 1200s, 4800s), aliquots (2 pmol of target protein each) were removed and mixed with pre-chilled quenching buffer (to a final concentration of 1M guanidine hydrochloride, 150 mM tris(2-carboxyethyl)phosphine, and 0.5% formic acid).

The quenched mixture was immediately loaded onto a homemade pepsin column for online digestion. The digested peptide mixtures were then loaded onto a reverse-phase column (Zorbax 300SB-C18, 0.3×5 mm; Agilent Technologies, Wilmington, Del., USA). The desalted peptides were then separated on a homemade column (LiChrospher 5 µm, 75 µm I.D. length 10 cm) using a linear gradient of 8%-95% HPLC buffer (99.9% acetonitrile/0.1% formic acid/0.025% Trifluoroacetic acid) for 10 minutes with a flow rate of 0.5 µl/min.

The LC apparatus was coupled to a 2D linear ion trap mass spectrometer (Orbitrap Classic; Thermo Fisher, San Jose, Calif., USA) operated with Xcalibur 2.2 software (Thermo Fisher, San Jose, Calif., USA). The full-scan MS was performed in the Orbitrap over a range of 350-1,600 Da and a resolution of 60,000 at m/z 400. Internal calibration was performed using the ion signal of $[Si(CH_3)_2O]_6H^+$ at m/z 536.165365 as a lock mass. The electrospray voltage was set to 0.2 kV, and the temperature of the capillary was set to 200° C. MS and MS/MS automatic gain control were set to 1,000 ms (full scan) and 120 ms (MS/MS), or $2\times10^6$ ions (full scan) and $3\times10^3$ ions (MS/MS) for maximum accumulated time or ions, respectively.

The peptide identifications were carried out using Proteome Discoverer software (version 1.4, Thermo Fisher Scientific). The MS/MS spectra were searched against the single protein database using the SEQUEST search engine. For peptide identification, 20 ppm mass tolerance was permitted for intact peptide masses, and 0.5 Da for CID fragment ions. Peptide-spectrum match (PSM) were then filtered based on high confidence and search engine rank 1 of peptide identification to ensure an overall false discovery rate below 0.01.

For HDX profile analysis, the peptide identification template was made based on the LC-MS/MS results of target protein identification. The template was then preloaded in ExMS module installed in MATLAB. The MS spectra of HDX were loaded and analyzed to calculate the number of incorporated deuterium for each peptide which was then presented as average numbers of deuterium incorporations of two independent experiments.

Reproducible results of duplicate HDX-MS experiments were selected to represent the HDX profiles. The two epitope regions were found in the peptide sequences RKGDVSL (SEQ ID NO: 9, residues 87-93 on TIM-3) and EKFNLKL (SEQ ID NO: 10, residues 119-125 on TIM-3), which showed lower deuterium incorporation in the presence of mouse monoclonal antibody, as compared to in the absence of the antibody (FIGS. 7A and 7B).

Figure 7A:
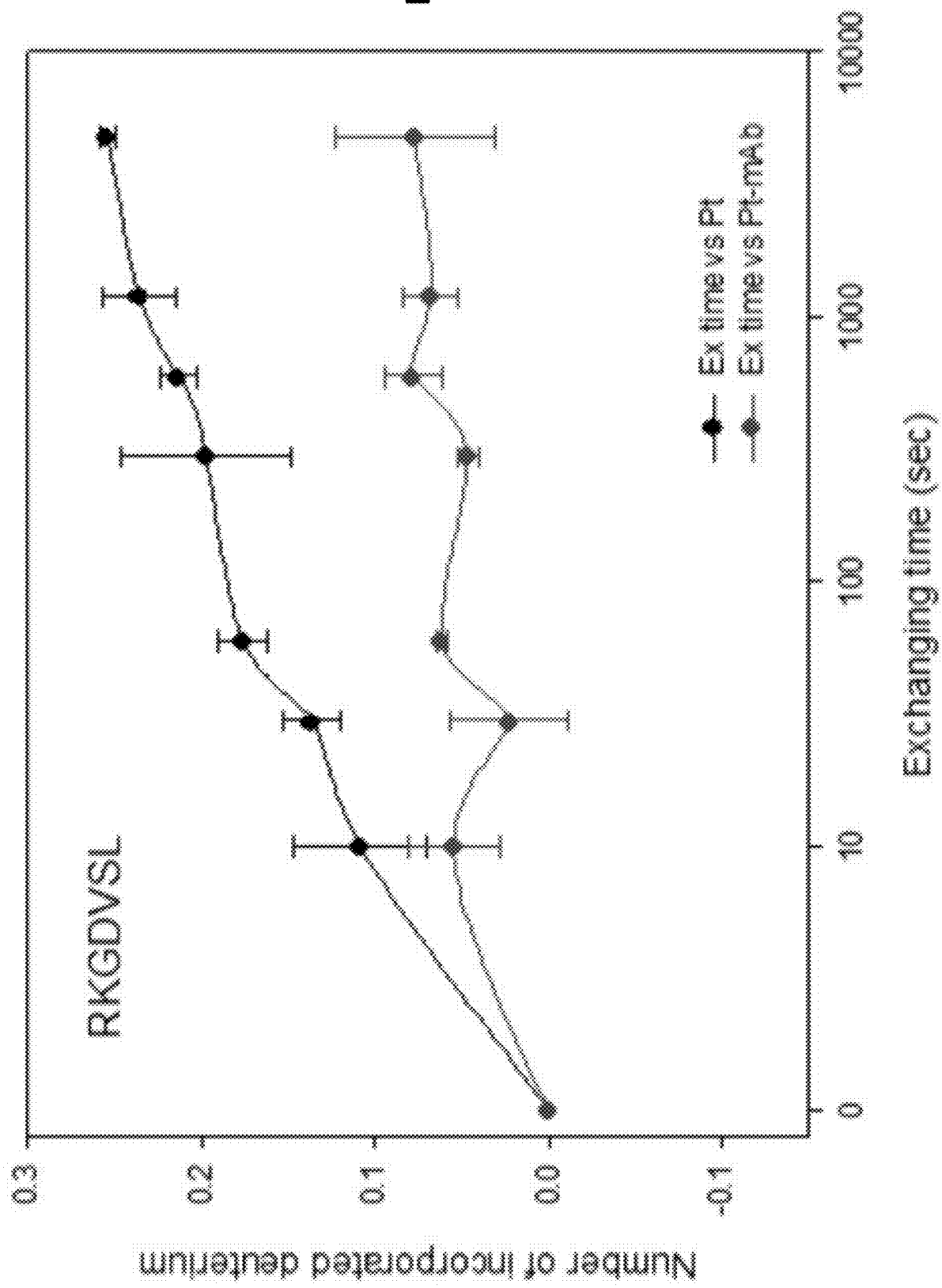
FIG. 7A and FIG. 7B show results from HDX-MS studies, which measure the hydrogen and deuterium exchange rates of peptide fragments in the absence or presence of anti-human TIM-3 antibody. Peptide fragments of the extra cellular domain of human TIM-3 were subjected to HDX in the presence or absence of the antibody. The HDX peptides were then analyzed with MS for the extents of deuterium exchanges. These results indicate that the anti-human TIM-3 antibody preferentially binds to two peptide regions in TIM-3, indicating that the epitopes are located in these two regions.

FIG. 7A shows the incorporation of deuterium in the peptide segment, RKGDVSL (SEQ ID NO: 9), as a function of time, in the presence and absence of antibody. The significantly slower incorporation rate in the presence of antibody, as compared to in the absence of antibody, indicates that this peptide segment is protected from solvent upon antibody binding. That is, this peptide segment is involved in antibody binding.

Figure 7B:
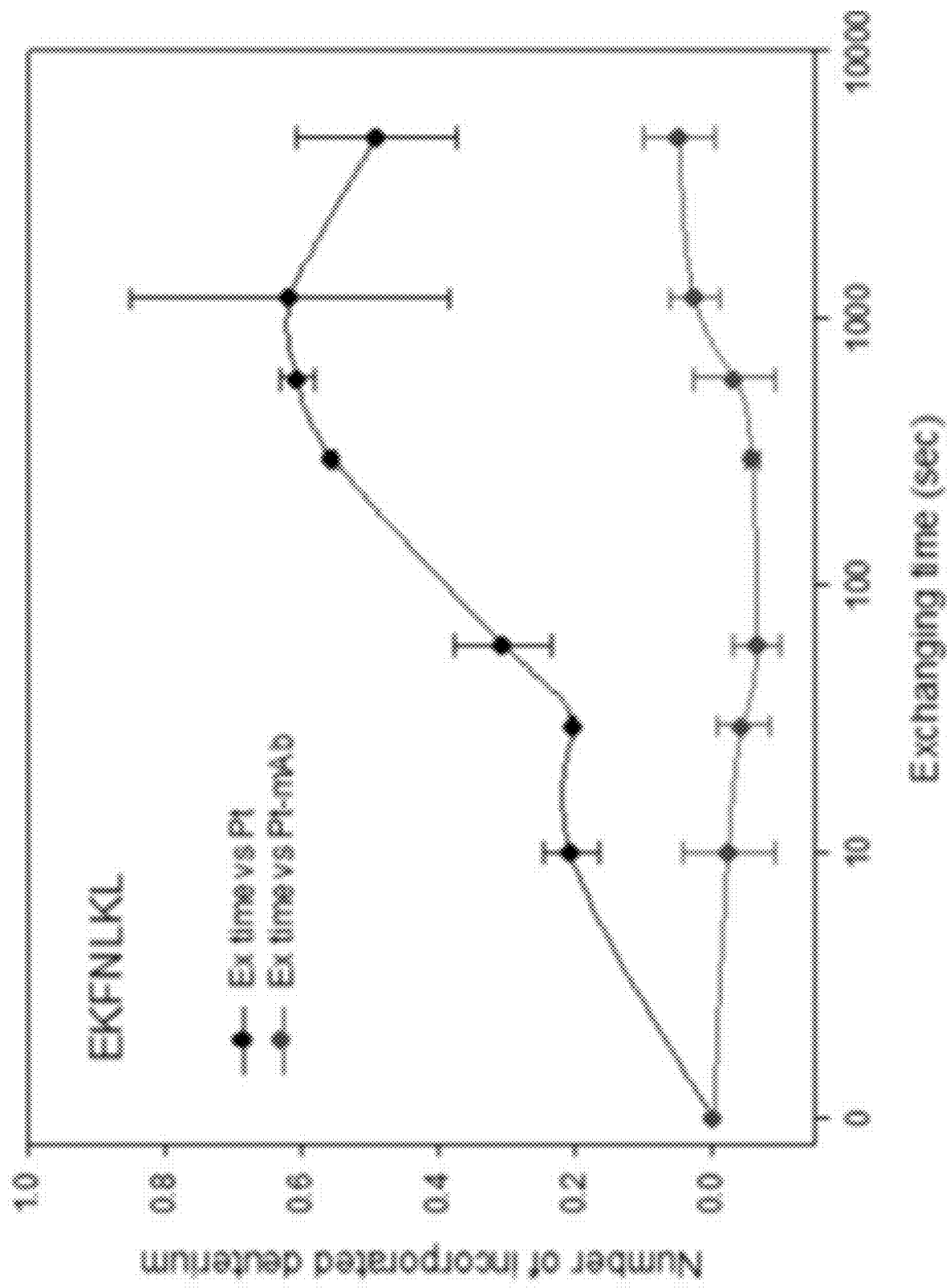

FIG. 7B shows incorporation of deuterium in the peptide segment, EKFNLKL (SEQ ID NO: 10), as a function of time, in the presence and absence of antibody. The significantly slower incorporation rate in the presence of antibody, as compared to in the absence of antibody, indicates that this peptide segment is protected from solvent upon antibody binding. That is, this peptide segment is involved in antibody binding.

From the above experiments, the binding epitopes for mAb 8C11 were found to be located in the regions spanning RKGDVSL (SEQ ID NO: 9) and EKFNLKL (SEQ ID NO: 10). To confirm that these regions include the mAb 8C11 binding epitopes and to investigate the residues within these regions that are important for mAb 8C11 bindings, we performed alanine scanning in these regions.

Figure 7C:
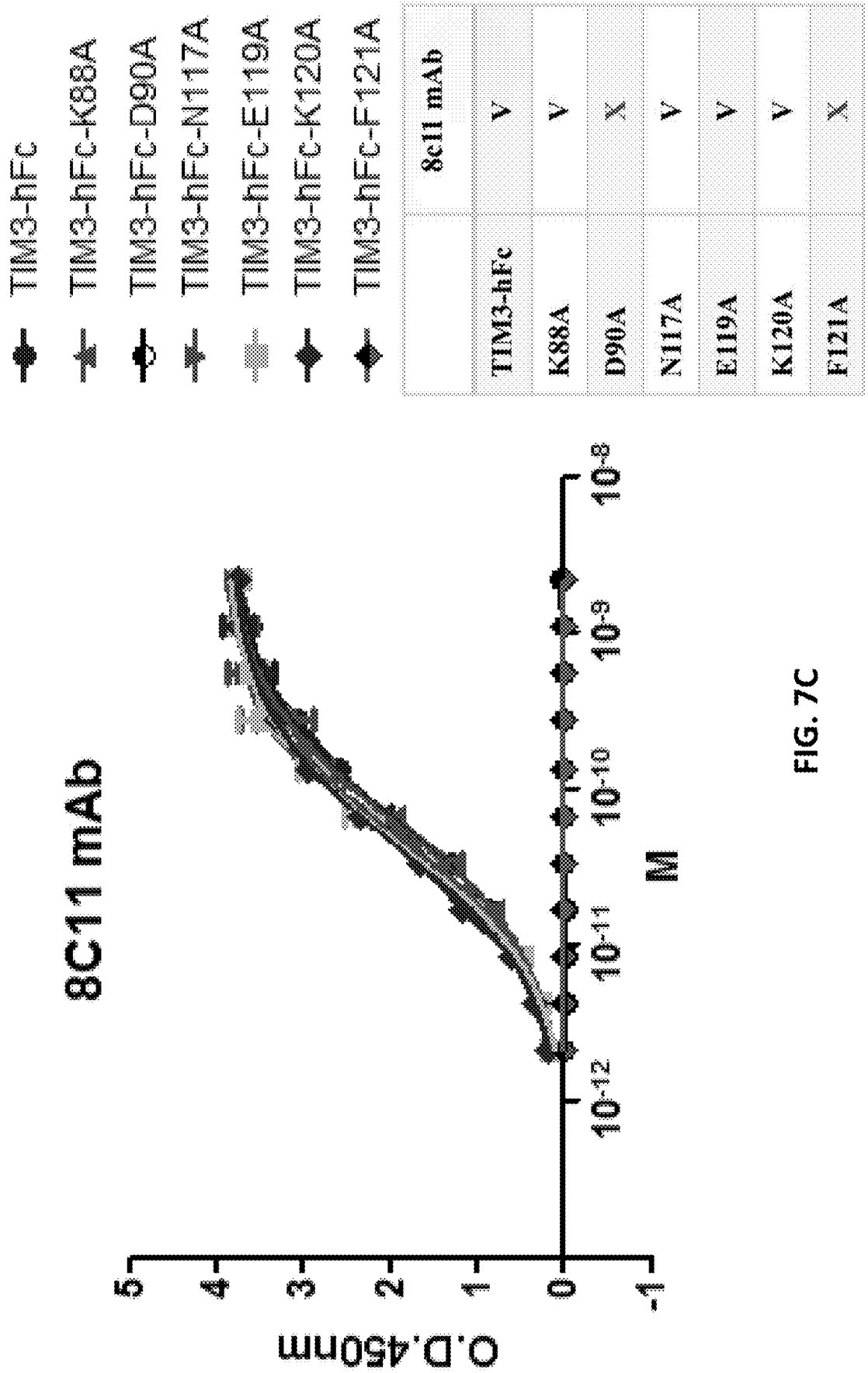
FIG. 7C shows results of analysis of effects of site-directed mutagenesis in TIM-3 mAb binding epitope regions on binding with mAb 8C11.

Results shown in FIG. 7C confirm that mAb 8C11 binding epitopes are indeed located in these regions. In addition, results from the alanine-scanning show that alanine substitutions at residues 90 (D90A) and 121 (F121A) abolished the binding of mAb 8C11 to TIM-3. In contrast, alanine-substitutions at residues 88 (K88A), 117 (N117A), 119 (E119A), and 120 (K120A) did not abolish the binding of mAb 2E28C11 to TIM-3. These results indicate that residues D-90 and F-121 are critical for mAb 8C11 binding to TIM-3.

Example 8: Anti-TIM-3 Antibody 8C11 Regulates the Section of IFN-γ and TNF-α by Human T Cells Exhausted T cells would not produce factors that are important for proper immune responses, such as TNF-α and IFN-γ. To test whether anti-TIM-3 antibodies of the invention can enhance the productions of these factors by the T cells, the following experiments were performed. Human CD4 or CD8 T cells were treated with or without antibodies and stimulated with CD3/CD28 dynamic beads for 3 days. The supernatants were then collected for further analysis with multiplex. The results show that the secretions of IFN-γ or TNF-α were increased in the treatment groups. The treatment groups with anti-TIM-3 mAb 8C11 show substantially greater increases, as compared with the anti-TIM-3 mAb 2E2 treatment groups.

Figure 8A:
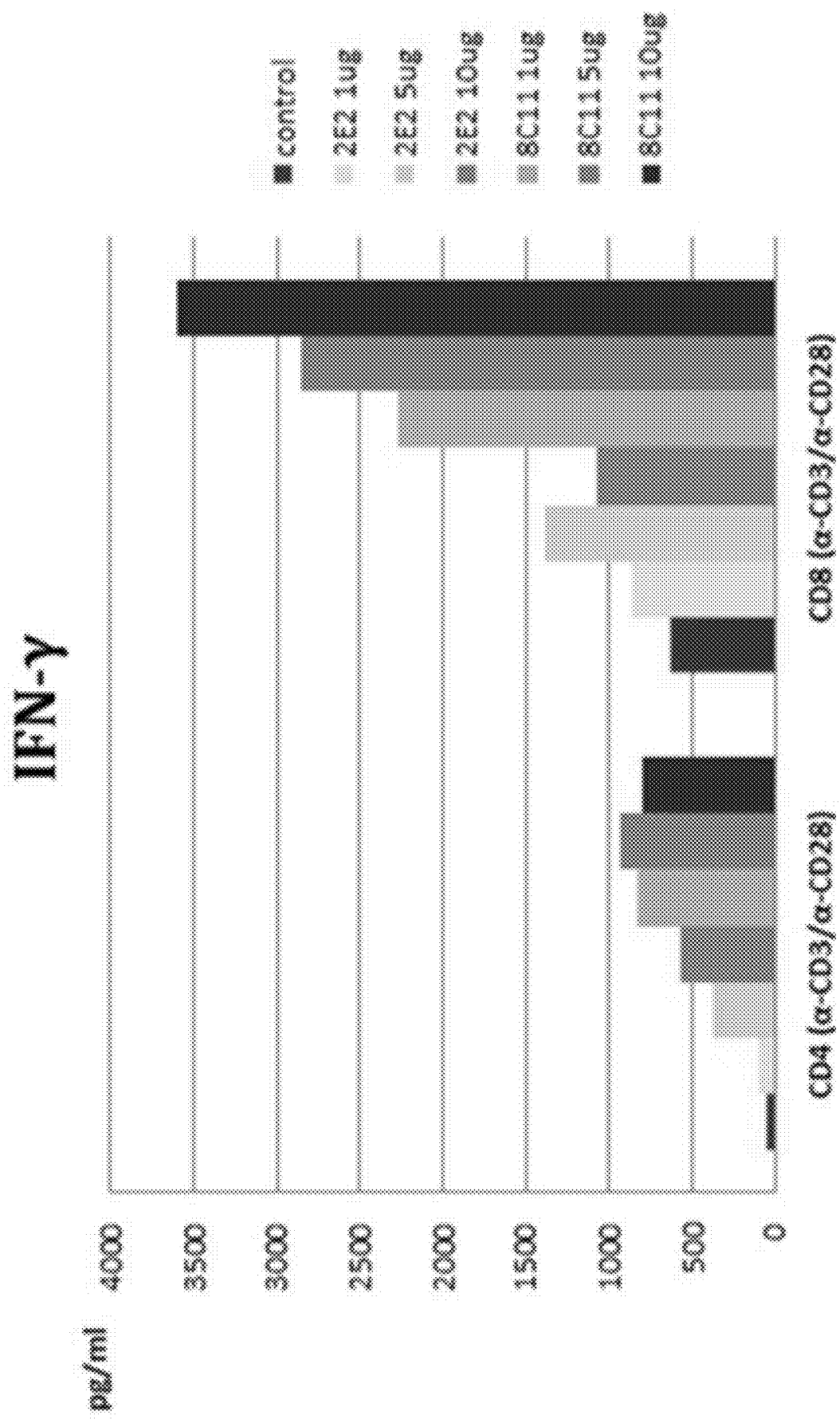
FIG. 8A shows that anti-TIM-3 mAb 8C11 enhances IFN-gamma secretion by human T cells.
Figure 8B:
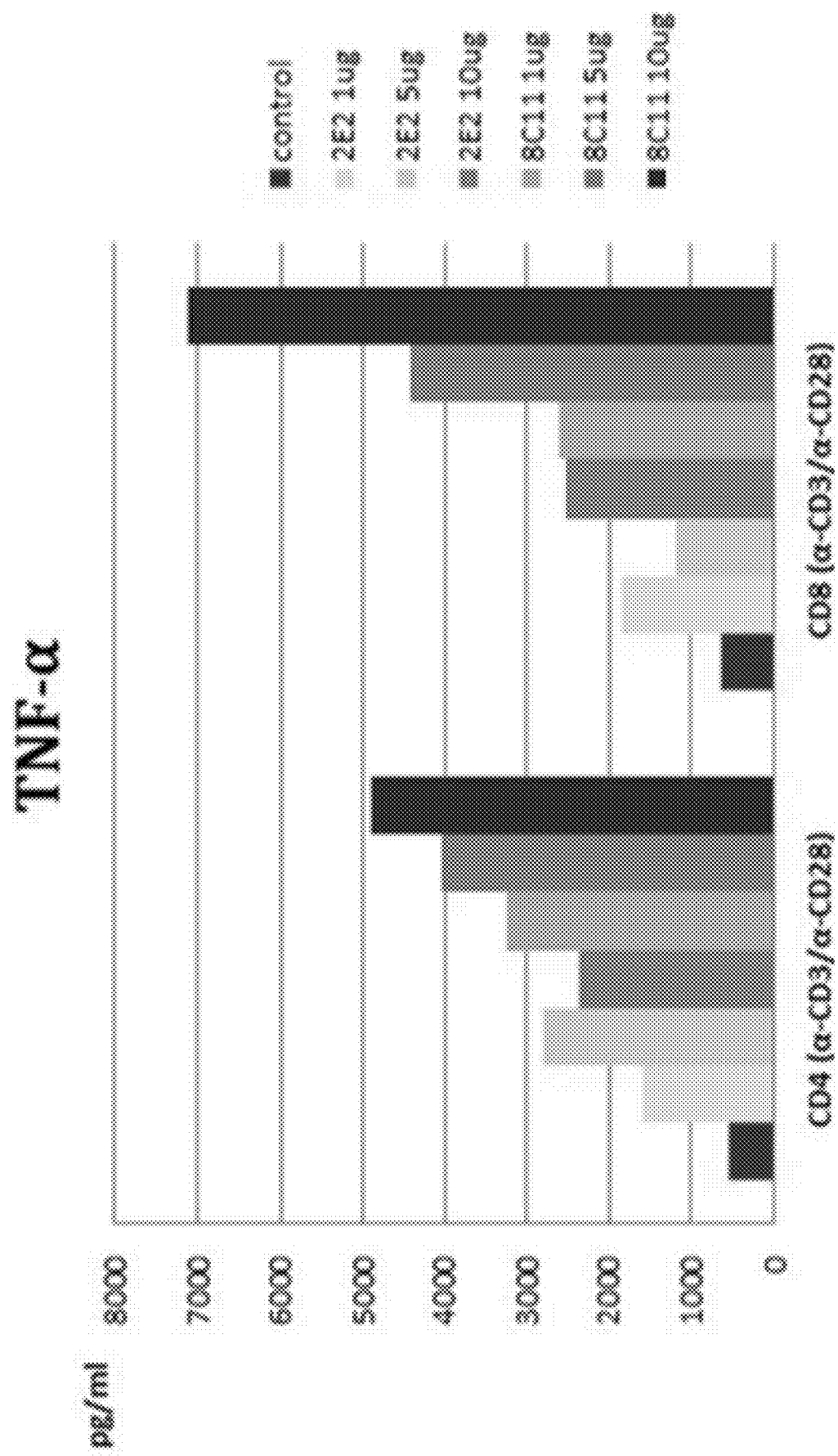
FIG. 8B shows that anti-TIM-3 mAb 8C11 enhances TNF-alpha secretion by human T cells.
Figure 9:
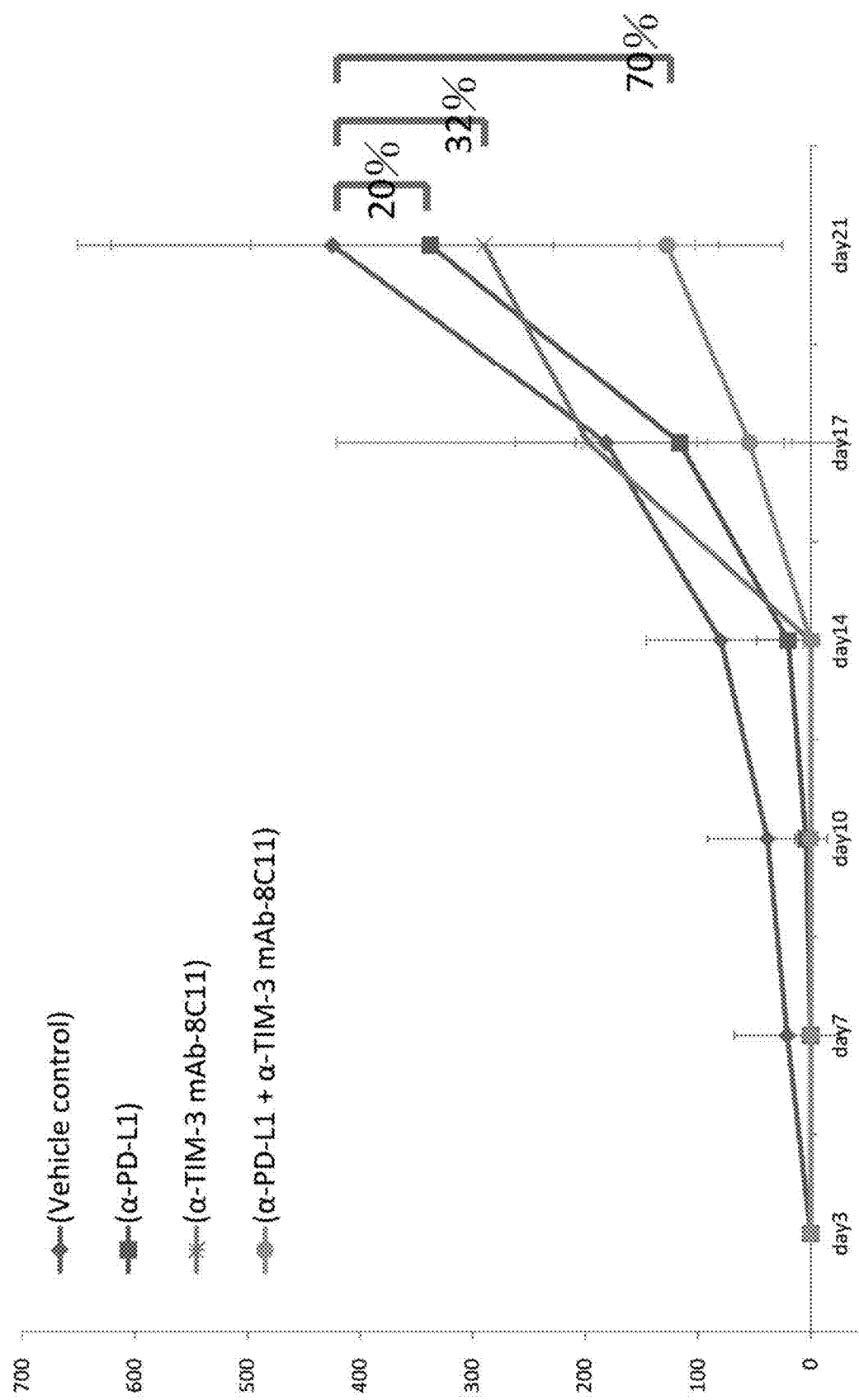
FIG. 9 shows therapeutic applications of anti-human TIM-3 antibody 8C11. Using an animal model, the anti-human TIM-3 antibody 8C11 is shown to inhibit melanoma growth. This therapeutic effect is even more pronounced when the treatment is combined with anti-PD-L1 antibody, due to a synergistic effect.

FIG. 8A shows that anti-TIM-3 mAb 8C11 treatment enhances IFN-γ secretion in human T cells. FIG. 8B shows that anti-TIM-3 mAb 8C11 treatment enhances TNF-α secretion in human T cells. These results indicate that an antibody of the invention may be used to prevent or reverse T cell exhaustion, thereby enhancing normal immune responses.

Example 9: Cloning of Gene Encoding the 8C11 Monoclonal Antibody

Cloning of the gene encoding the 8C11 mAb is performed in accordance with the methods described below. While the following procedures may set out specific conditions and parameters, one skilled in the art would appreciate that this is only an example for illustrating embodiments of the invention and that other modifications and variations are possible without departing from the scope of the invention.

cDNA Cloning of Antibody Genes and Preparation

The hybridoma was culture in a defined medium. When the cell number reached about 10×10$^6$ cells/ml, the cells were harvested by centrifugation, and then TRIzol kit was added to extract total RNA in accordance the instruction manual. Cloning the variable regions of the antibody cDNAs was performed using a mouse Ig-primer set in accordance with the instruction manual from the supplier. The first strand cDNA was prepared using 5 micrograms of total RNA as a template, 50 ng/ml of random primers, and 10 μM dNTP, which were mixed in DEPC-water in a PCR tube.

The reaction mixture was incubated at 65° C. for 5 min, and then placed on ice. Ten (10) μl cDNA synthesis mixture containing 2 μl of 10× RT buffer, 4 μl of 25 mM MgCl$_2$, 2 μl of DTT, 1 μl of 4 units of RNaseOUT, and 1 μl of 200 units of SuperScript III RT, was mixed gently and collected by brief centrifugation. The reaction tube was incubated for 10 min at 25° C., followed by 50 min at 50° C. The reaction was terminated by heating at 85° C. for 5 min and then the tube was chilled on ice. The tube was briefly centrifuged to collect the reaction product, and 1 μl of RNase H was added and the mixture was incubated for 20 min at 37° C.

A reaction mixture having a composition of 5 μl of cDNA, 5 μl of 10× reaction buffer, 1 μl of 10 mM dNTP mix, 1 μl of 2.5 unit Taq polymerase, and 1 μl of forward and reverse primer were prepared in a final volume of 50 μl with double distilled water and subjected to PCR. For amplification of the light chain and heavy chain of an antibody, 94° C. as the first step, and then a cycle of 94° C. for 30 sec, 55° C. for 30 sec, and 72° C. as 1 min was repeated 30 times. After the reaction cycles, the final step was 72° C. for 10 min. The reaction mixture was analyzed by 2% agarose gel. Products with the predicted molecular weights were ligated into a cloning vector, and then used to determine the nucleotide sequences.

Based on the sequence information, antibody sequences were translated into protein sequences using the ExPASY-Translation tool. Resulting sequences of anti-human TIM-3 antibody 8C11 comprise a heavy chain amino acid sequence and a light chain sequence. The complementarity determining regions (CDR) in these sequences were determined by the method of Kabat et al., Sequences of proteins of immunological interest, Fifth Edition, NIH Publication 91-3242, Bethesda Md. (1991), vols. 1-3.

FIG. 1. Depicts the amino acid sequences of 8C11 antibody variable heavy chain region (SEQ ID NO:1) and light chain region (SEQ ID NO:2). The framework regions (FR1, FR2, FR3, and FR4) and CDRs (HCDR1 SEQ ID NO:3, HCDR2 SEQ ID NO:4, HCDR3 SEQ ID NO:5, LCDR1 SEQ ID NO:6, LCDR2 SEQ ID NO:7, and LCDR3 SEQ ID NO:8) are indicated.

Example 10: The Xenograft Animal Model Illustrates the Ability of Tumor Growth Inhibition by Anti-Human TIM-3 Antibody 8C11

Tumor growth is often associated with T cell exhaustion. T cell exhaustion results in reduced immune responses, which permit the cancer cells to grow unchecked. Because anti-TIM-3 antibodies are found to reverse or minimize the conditions of T cell exhaustion, e.g., blocking Galectin-9/ TIM-3 binding and enhancing the secretions of IFN-γ and TNF-α by T cells, it is likely that these antibodies can prevent or slow the growth of cancer cells. To test this, the following experiment was performed.

NOD.Cg-Prkdc$^{scid}$Il2rg$^{tm1wjl}$/YckNarl mice (5 to 6-week-old) were injected with 0.5×10$^6$ human fresh PBMCs i.p. and a total of 10$^6$ A375 human melanoma cells were injected subcutaneously (s.c.) in 50 μL of PBS on day 0 of the experiment. Mice were treated with anti-TIM-3 mAb (8C11, 5 mg/kg per injection), anti-hPD-L1 mAb (8 mg/kg per injection), Combo (anti-TIM-3, 8C11, 5 mg/kg plus anti-hPD-1, 8 mg/kg per injection each), or saline control.

Mice were administered by i.p. injection on days 0, 2, 4 for antibody against TIM-3, and on day 0, 3, 6, 9, 12 for antibody against PD-L1. Survival and xenograft-versus-host reaction were monitored daily up to 28 days. Animals that developed clinical symptoms of xenogeneic graft versus host disease (xGVHD) (>15% weight loss, hunched posture, reduced mobility, fur loss, tachypnea) were sacrificed, and an endpoint of survival was recorded. Mice were sacrificed on day 25 and s.c. tumors were removed, weighed, and processed for immune histochemistry (IHC) and FACS analysis.

The results indicated that by day 21, anti-human TIM-3 antibody 8C11 treatment alone reduced the tumor growth by about 30%, and anti-hPD-L1 treatment alone reduced the tumor growth inhibition by about 20%. However, the combined treatment with anti-hPD-L1 reduced tumor growth by about 70%. These results indicate that the antibody against TIM-3 is more effective than the antibody against PD-L1 in inhibiting tumor cell growth. More importantly, these results show that there is a synergistic effect in the combination treatment with anti-human TIM-3 antibody 8C11 and anti-hPD-L1. Because PD-1 and TIM-3 are the two major receptors found to be involved in T cell exhaustion, the anti-TIM-3 antibody, alone or together with an anti-PD-1 antibody, would be useful in counter T cell exhaustion, and therefore can be used to treat diseases or conditions involving immune suppression (T cell exhaustion).

Some embodiments of the invention relate to the uses of antibodies of the invention in treating diseases or disorders associated with T cell exhaustion mediated by TIM-3. Such diseases include cancers, such as lung, breast, pancreas, liver, colorectal, or prostate cancers. In accordance with embodiments of the invention, a method for treating such cancer may comprise administering an effective amount of an antibody of the invention to a subject in need thereof. An effective amount is the amount needed to effect the treatments. One skilled in the art would appreciate that the effective amount would depend on the disease, the patient (age, weight), dosage form, route of administration, etc. One skilled in the art can determine the effective amount without undue experimentation. The administration may be by any suitable means, including injections, such as subcutaneous injection, intramuscular injection, intravenous injection, intraperitoneal injection, etc.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An anti-human T-cell immunoglobulin domain and mucin domain 3 (TIM-3) antibody, or binding fragment thereof, wherein the antibody or the binding fragment comprises a heavy-chain variable domain having the following complementarity determining region (CDR) sequences: HCDR1 (SEQ ID NO: 3), HCDR2 (SEQ ID NO: 4), HCDR3 (SEQ ID NO: 5), and a light-chain variable domain having the following CDR sequences: LCDR1 (SEQ ID NO: 6), LCDR2 (SEQ ID NO: 7), and LCDR3 (SEQ ID NO: 8).

2. The anti-human T-cell immunoglobulin domain and mucin domain 3 (TIM-3) antibody, or the binding fragment thereof, according to claim 1, wherein the heavy chain comprises the sequence of SEQ ID NO: 1.

3. The anti-human T-cell immunoglobulin domain and mucin domain 3 (TIM-3) antibody, or the binding fragment thereof, according to claim 1, wherein the light chain comprises the sequence of SEQ ID NO: 2.

4. The anti-human T-cell immunoglobulin domain and mucin domain 3 (TIM-3) antibody, or the binding fragment thereof, according to claim 1, wherein the heavy chain comprises the sequence of SEQ ID NO: 1 and the light chain comprises the sequence of SEQ ID NO: 2.

5. A pharmaceutical composition comprising an anti-human T-cell immunoglobulin domain and mucin domain 3 (TIM-3) antibody, or binding fragment thereof, wherein the antibody or the binding fragment comprises a heavy-chain variable domain having the following complementarity determining region (CDR) sequences: HCDR1 (SEQ ID NO: 3), HCDR2 (SEQ ID NO: 4), HCDR3 (SEQ ID NO: 5), and a light-chain variable domain having the following CDR sequences: LCDR1 (SEQ ID NO: 6), LCDR2 (SEQ ID NO: 7), and LCDR3 (SEQ ID NO: 8).

6. The pharmaceutical composition according to claim 5, wherein the heavy chain comprises the sequence of SEQ ID NO: 1.

7. The pharmaceutical composition according to claim 5, wherein the light chain comprises the sequence of SEQ ID NO: 2.

8. The pharmaceutical composition according to claim 5, wherein the heavy chain comprises the sequence of SEQ ID NO: 1 and the light chain comprises the sequence of SEQ ID NO: 2.

* * * * *